(12) United States Patent
Bradford et al.

(10) Patent No.: US 8,754,109 B2
(45) Date of Patent: *Jun. 17, 2014

(54) PIRFENIDONE THERAPY AND INDUCERS OF CYTOCHROME P450

(75) Inventors: Williamson Z. Bradford, Ross, CA (US); Javier Szwarcberg, San Francisco, CA (US)

(73) Assignee: Intermune, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/513,472

(22) PCT Filed: Dec. 3, 2010

(86) PCT No.: PCT/US2010/058936
§ 371 (c)(1),
(2), (4) Date: Oct. 11, 2012

(87) PCT Pub. No.: WO2011/069089
PCT Pub. Date: Jun. 9, 2011

(65) Prior Publication Data
US 2013/0045997 A1 Feb. 21, 2013

(30) Foreign Application Priority Data

Mar. 3, 2010 (EP) .................................. 10250378
Oct. 8, 2010 (CA) .................................. 2710014

(51) Int. Cl.
*A01N 43/40* (2006.01)
*A61K 31/44* (2006.01)

(52) U.S. Cl.
USPC ........................... 514/350; 514/354; 514/345

(58) Field of Classification Search
USPC ......................................... 514/350, 354, 345
See application file for complete search history.

(56) References Cited

U.S. PATENT DOCUMENTS

| | | | |
|---|---|---|---|
| 5,310,562 | A | 5/1994 | Margolin |
| 5,518,729 | A | 5/1996 | Margolin |
| 5,716,632 | A | 2/1998 | Margolin |
| 7,407,973 | B2 | 8/2008 | Ozes et al. |
| 7,566,729 | B1 | 7/2009 | Bradford et al. |
| 7,605,173 | B2 | 10/2009 | Seth |
| 8,084,475 | B2 | 12/2011 | Bradford et al. |
| 2006/0110358 | A1 | 5/2006 | Hsu |
| 2007/0053877 | A1 | 3/2007 | Crager et al. |
| 2007/0054842 | A1 | 3/2007 | Blatt et al. |
| 2007/0072181 | A1 | 3/2007 | Blatt |
| 2007/0092488 | A1 | 4/2007 | Strieter et al. |
| 2007/0117841 | A1 | 5/2007 | Ozes et al. |
| 2007/0172446 | A1 | 7/2007 | Blatt |
| 2007/0203202 | A1 | 8/2007 | Robinson et al. |
| 2007/0203203 | A1 | 8/2007 | Tao et al. |
| 2008/0019942 | A1 | 1/2008 | Seiwert et al. |
| 2008/0194644 | A1 | 8/2008 | Bradford |
| 2008/0287508 | A1 | 11/2008 | Robinson et al. |
| 2009/0170804 | A1 | 7/2009 | Phillips et al. |
| 2009/0197923 | A1 | 8/2009 | Bradford |
| 2011/0136876 | A1 | 6/2011 | Robinson et al. |

FOREIGN PATENT DOCUMENTS

EP          1138329         10/2001

OTHER PUBLICATIONS

Raghu et al. American Journal Of Respiratory And Critical Medicine, vol. 159 (1999), pp. 1061-1069.*
Shimizu et al. 1998, Kidney International, vol. 54, pp. 99-109.*
U.S. Appl. No. 13/857,465, filed Apr. 2013, Robinson et al.*
U.S. Appl. No. 13/326,971, filed Dec. 2011, Bradford et al.*
Antoniu et al., Pirfenidone for the treatment of idiopathic pulmonary fibrosis, Expert Opin. Investigational Drugs, 15:823-8 (2006).
Azuma et al., Double-blind, placebo-controlled trial of pirfenidone in patients with idiopathic pulmonary fibrosis, Am. J. Respir. Crit. Care Med., 117:1040-7 (2005).
Branch et al., In vivo modulation of CYP enzymes by quinidine and rifampin, Clin. Pharmacol. Ther., 68:401-11 (2000).
Correspondence received from FDA.
Cytochrome P450 Drug Interaction Table, Version 5.0 released on Jan. 12, 2009, Indiana University School of Medicine.
Eldon et al., Lack of effect of withdrawal from cigarette smoking on theophylline pharmacokinetics, J. Clin. Pharmacol., 27:221-5 (1987).
English translation of collection of Review Reports from Japanese Pharmaceuticals and Medical Devices Agency (PMDA) review of Shionogi & Co., Ltd.'s Pirespa Tablet product (dates, Sep. 16, 2008, Sep. 8, 2008, Aug. 20, 2008, and Jul. 4, 2008) (http://www.pmda.go.jp/english/service/pdf/Pirespa-Pirfenidone.pdf).
Examination Report for European Patent Application No. 10 250 378.6, European Patent Office, dated Jun. 11, 2010.
Faber et al., Time response of cytochrome P450 1A2 activity on cessation of heavy smoking, Clin. Pharmacol. Ther., 76:178-84 (2004).
Food and Drug Administration Center for Drug Evaluation and Research, Pulmonary-Allergy Drugs Advisory Committee (PADAC) Meeting Transcript (Tuesday, Mar. 9, 2010), published at http://www.fda.gov/downloads/AdvisoryCommittees/CommitteesMeetingMaterials/Drugs/Pulmonary-AllergyDrugsAdvisoryCommittee/UCM208806.pdf.
Hemeryck et al., Selective serotonin reuptake inhibitors and cytochrome P-450 mediated drug-drug interactions: an update, Curr. Drug Metab., 3:13-37 (2007).
International Preliminary Report on Patentability for corresponding international application PCT/US2010/058936, dated Jun. 5, 2012.
International Search Report and Written Opinion for PCT/US2010/058936 dated Feb. 1, 2011.
Jeppesen et al., Dose-dependent inhibition of CYP1A2, CYP2C19 and CYP2D6 by citalopram, fluoxentine, fluvoxamine and paroxetine, Eur. J. Clin. Pharmacol. 51(1): 73-8 (1996).
Kroon, Drug interactions with smoking, Am. J. Health-Syst. Pharm. 64:1917-21 (2007).

(Continued)

*Primary Examiner* — Kara R McMillian
(74) *Attorney, Agent, or Firm* — Carolyn Tang; John Bendrick; Marshall, Gerstein & Borun LLP

(57) ABSTRACT

The present invention relates to methods involving avoiding adverse drug interactions with pirfenidone and CYP inducers, such as smoking.

19 Claims, 1 Drawing Sheet

(56) References Cited

OTHER PUBLICATIONS

Landi et al., Human cytochrome P4501A2, Metabolic Polymorphisms and Susceptibility of Cancer, Chapter 16, pp. 173-195 (1999).

Pirfenidone NDA 22-535 Pulmonary-Allergy Drugs Advisory Committee Mar. 9, 2010, slide deck (InterMune, Inc.), published at http://www.fda.gov/downloads/AdvisoryCommittees/CommitteesMeetingMaterials/Drugs/Pulmonary-AllergyDrugsAdvisoryCommittee/UCM206399.pdf.

Pulmonary-Allergy Drugs Advisory Committee Meeting, Pirfenidone Capsules, NDA 22-535, S-000, Mar. 9, 2010, slide deck (U.S. Food and Drug Administration), published at http://www.fda.gov/downloads/AdvisoryCommittees/CommitteesMeetingMaterials/Drugs/Pulmonary-AllergyDrugsAdvisoryCommittee/UCM206398.pdf.

Remington's: The Science and Practice of Pharmacy, 17th Edition, vol. 1, p. 806 (1985).

Scriabine et al., New developments in the therapy of pulmonary fibrosis, Adv. Pharmacol., 57:419-64 (2009).

Shionogi & Co. Ltd., Pirespa Tablet Packaging Label, Prepared in Oct. 2008.

Smoking and Drug Interactions, Medicines Information Centre Pharmacy Department UKMI, Jun. 2007.

Taniguchi et al., ERJ Express, published online as doi:10.1183/09031936.00005209 on Dec. 8, 2009.

Zevin et al., Drug interactions with tobacco smoking: an update, Clin. Pharmacokinet., 36(6):425-38 (1999).

Sponsor's Briefing Document for the FDA Pulmonary-Allergy Drugs Advisory Committee (PADAC) Meeting for pirfenidone, published at http://www.fda.gov/downloads/AdvisoryCommittees/CommitteesMeetingMaterials/Drugs/Pulmonary-AllergyDrugsAdvisoryCommittee/UCM203083.pdf.

* cited by examiner

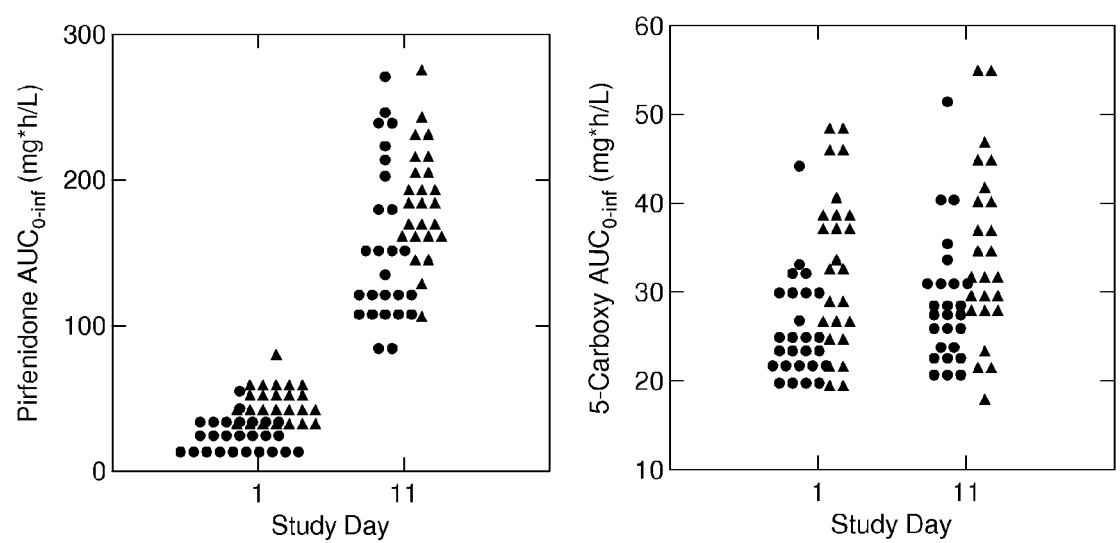

PIRFENIDONE THERAPY AND INDUCERS OF CYTOCHROME P450

FIELD OF THE INVENTION

The invention relates to improved methods of administering pirfenidone therapy, involving increased effectiveness of pirfenidone through the avoidance of inducers of cytochrome P450 (CYP) proteins which metabolize pirfenidone. More specifically, the invention is related to methods of administering pirfenidone therapy involving the avoidance of inducers of CYP1A2.

BACKGROUND

Pirfenidone is small drug molecule whose chemical name is 5-methyl-1-phenyl-2-(1H)-pyridone. It is a non-peptide synthetic molecule with a molecular weight of 185.23 daltons. Its chemical elements are expressed as $C_{12}H_{11}NO$, and its structure and synthesis are known. Pirfenidone is manufactured commercially and being evaluated clinically as a broad-spectrum anti-fibrotic drug. Pirfenidone has anti-fibrotic properties via: decreased TGF-β expression, decreased TNF-α expression, decreased PDGF expression, and decreased collagen expression.

Pirfenidone is being investigated for therapeutic benefits to patients suffering from fibrosis conditions such as Hermansky-Pudlak Syndrome (HPS) associated pulmonary fibrosis and idiopathic pulmonary fibrosis (IPF). Pirfenidone is also being investigated for a pharmacologic ability to prevent or remove excessive scar tissue found in fibrosis associated with injured tissues including that of lungs, skin, joints, kidneys, prostate glands, and livers. Published and unpublished basic and clinical research suggests that pirfenidone may safely slow or inhibit the progressive enlargement of fibrotic lesions, and prevent formation of new fibrotic lesions following tissue injuries.

As an investigational drug, pirfenidone is provided in tablet and capsule forms principally for oral administration. Various formulations have been tested and adopted in clinical trials and other research and experiments. The most common adverse reactions or events associated with pirfenidone therapy (>10%) are nausea, rash, dyspepsia, dizziness, vomiting, and photosensitivity reaction, and anorexia. Many of these effects can interfere with everyday activities and quality of life. These effects appear to be dose related. The adverse reactions associated with pirfenidone therapy are exacerbated when pirfenidone is administered at higher doses. In comparison to studies performed to determine the effects of pirfenidone therapy on patients, relatively little was known about the effects of pirfenidone when used in combination with other therapeutics.

Pirfenidone has been shown to be metabolized by isoforms of the cytochrome P450 (CYP) protein (Report on the Deliberation Results, Evaluation and Licensing Division, Pharmaceutical and Food Safety Bureau, Ministry of Health Labour and Welfare, Sep. 16, 2008). Specifically, several CYP isoforms (CYP1A2, 2C9, 2C19, 2D6 and 2E1) were involved in the earliest stages of oxidative metabolism of pirfenidone.

Activity of CYPs in patients who smoke is significantly increased over their non-smoking counterparts.

SUMMARY

The invention disclosed herein is based upon the discovery of an adverse reaction (reduced pirfenidone exposure) in patients taking pirfenidone who also smoke.

The invention generally relates to improved methods of administering pirfenidone to a patient in need of pirfenidone therapy, and to methods of preparing or packaging pirfenidone medicaments, containers, packages and kits. In any of the aspects or embodiments, the patient can have idiopathic pulmonary fibrosis (IPF) and the medicament is for treatment of IPF. In any of the aspects or embodiments, the therapeutically effective amount of pirfenidone being administered can be a daily dosage of at least 1800 mg, or 2400 mg or 2403 mg per day. In any of the aspects of the invention, the daily dosage can be administered in divided doses three times a day, or two times a day, or alternatively is administered in a single dose once a day. In any of the aspects of the invention, the pirfenidone can be administered with food. For example, the daily dosage of 2400 mg or 2403 mg pirfenidone per day can be administered as follows: 800 mg or 801 mg taken three times a day, with food.

In some aspects, the invention provides a method of administering pirfenidone therapy to a patient in need of pirfenidone therapy (e.g., a patient with IPF), involving administering to the patient a therapeutically effective amount of pirfenidone, and avoiding use or administration of an inducer of a cytochrome P450 (CYP) that metabolizes pirfenidone ("CYP inducer"). In some cases, the use or administration of the CYP inducer is avoided for at least 2.5 hours after administration of the pirfenidone. In various cases, the CYP that metabolizes pirfenidone is cytochrome P450 1A2 (CYP1A2). In some embodiments, the CYP inducer is a strong CYP1A2 inducer. Induction of CYP1A2 activity has been reported as a consequence of cigarette smoking, dietary factors, several drugs, chronic hepatitis, and exposure to polybrominated biphenyls and 2,3,7,8-tetrachlorodibenzo-p-dioxin. Landi et al. IARC Sci Publ. 1999; (148):173-95. In addition to, or in the alternative to smoking, the CYP inducers to be discontinued or avoided can be selected from the group consisting of carbamazepine, esomeprazole, griseofulvin, insulin, lansprazole, moricizine, omeprazole, rifampin, and ritonavir. The CYP inducers to be discontinued or avoided can additionally or alternatively be charbroiled foods and/or cruciferous vegetables. The CYP inducers to be discontinued or avoided can additionally or alternatively be selected from the group consisting of phenobarbital, phenyloin, primidone, and St. John's wort.

In other aspects, the invention provides a method of administering pirfenidone therapy to a patient in need of pirfenidone therapy, comprising discontinuing use or administration of an inducer of a CYP that metabolizes pirfenidone, e.g. a strong CYP1A2 inducer, to avoid an adverse drug interaction (e.g. or to avoid reduced exposure to pirfenidone) and administering a therapeutically effective amount of pirfenidone. In one embodiment, the patient discontinues use or administration of the CYP inducer concurrent with starting administration of pirfenidone. In another embodiment, the use or administration of the CYP inducer is discontinued within at least 3 days to within 4 weeks prior to or after starting pirfenidone therapy. This time period can, for example, permit adequate time for tapering and withdrawal without adverse effects, if such tapering is useful for the CYP inducer. In one example, in a method of administering a therapeutically effective amount of pirfenidone to a patient with IPF, the invention provides an improvement that comprises avoiding or discontinuing administration of a CYP inducer that metabolizes pirfenidone and administering a therapeutically effective amount of pirfenidone. In some embodiments, when the patient is a smoker (e.g., has not quit smoking), the patient avoids smoking for at least 2.5 hours after administration of pirfenidone.

In some embodiments, the patient is a smoker who is discontinuing smoking. In various embodiments, the method or use further comprises administering to the smoker patient a nicotine replacement therapy or other smoking cessation therapy. The nicotine replacement therapy can comprise one or more of a nicotine patch, a nicotine gum, a nicotine lozenge, a nicotine nasal spray, and a nicotine inhaler. The method can additionally or alternatively comprise administering buproprion hydrochloride (Zyban®) or varenciline (Chantix®).

Thus, an aspect of the invention provides pirfenidone for use in treating a patient in need of pirfenidone therapy, characterized in that the treating comprises avoiding, discontinuing, or contraindicating concomitant use or co-administration of a strong inducer of cytochrome P450 1A2 (CYP1A2). The concomitant use or co-administration is avoided, discontinued or contraindicated, in order to avoid the reduced (decreased) exposure to pirfenidone, or the potential for reduced exposure to pirfenidone. Administration of pirfenidone in patients that concomitantly smoke results in about 50% decrease in pirfenidone exposure ($AUC_{0-\infty}$), on average, compared to patients that do not smoke. It is understood that any of the aspects or embodiments or examples described herein with respect to methods of treatment apply to this aspect of the invention that provides pirfenidone for use in treating a patient. For example, the patient may be a patient with IPF, and the therapeutically effective amount administered may be at least 1800 mg, or 2400 or 2403 mg per day. As another example, the strong CYP1A2 inducer may be any known in the art or any of the strong CYP1A2 inducers described herein.

Similarly, a further related aspect of the invention provides the use of pirfenidone in the manufacture of a medicament for treating a patient in need of pirfenidone therapy, characterized in that the treating comprises avoiding, discontinuing, or contraindicating concomitant use or co-administration of a strong inducer of cytochrome P450 1A2 (CYP1A2) to avoid reduced exposure to pirfenidone. It is understood that any of the aspects or embodiments or examples described herein with respect to methods of treatment apply to this aspect of the invention that provides for the use of pirfenidone in manufacture of a medicament. For example, the patient may be a patient with IPF, and the therapeutically effective amount administered may be at least 1800 mg, or, more specifically 2400 or 2403 mg per day. As another example, the strong CYP1A2 inducer may be any known in the art or any of the strong CYP1A2 inducers described herein.

As used herein, "concomitant use" is understood to be interchangeable with concurrent administration or co-administration. Thus, the terms are understood to encompass administration simultaneously, or at different times, and by the same route or by different routes, as long as the two agents are given in a manner that allows both agents to be affecting the body at the same time. For example, concomitant use can refer to a medication concomitantly administered, whether prescribed by the same or a different practitioner, or for the same or a different indication.

In some embodiments, the patient is a patient in need of therapy with a CYP1A2 inducer, e.g. a strong CYP1A2 inducer. In some embodiments, the patient is a patient who was or is a smoker. In some embodiments, the patient is a patient who was a smoker immediately prior to starting administration of pirfenidone. In some embodiments, the patient in need of pirfenidone therapy is a patient avoiding concomitant use or co-administration of a strong inducer of cytochrome P450 1A2 (CYP1A2). In some embodiments, the patient is a patient who has been or is a smoker, and the patient is avoiding smoking when using pirfenidone. In some embodiments, the patient in need of pirfenidone therapy is a smoker who is discontinuing smoking to avoid reduced exposure to pirfenidone. In exemplary embodiments, the patient discontinues smoking within 4 weeks prior to the administration of pirfenidone, or concurrent with the start of administration of pirfenidone. It is understood that any of the aspects or embodiments or examples described herein with respect to methods of treatment apply to this aspect of the invention that provides for characterization of the patients to be treated with pirfenidone.

In yet other aspects, a method of administering pirfenidone therapy to a patient in need of pirfenidone comprises administering a therapeutically effective amount of pirfenidone to the patient, and any one, two, three, or more of the following:

(a) advising the patient that CYP inducers that metabolize pirfenidone should be avoided or discontinued or that inducers of CYP that metabolize pirfenidone are contraindicated;

(b) advising the patient that smoking should be avoided or discontinued;

(c) advising the patient that co-administration of pirfenidone with a CYP inducer that metabolizes pirfenidone can alter the therapeutic effect of pirfenidone;

(d) advising the patient that administration of pirfenidone in patients that smoke results in a 50% decrease in pirfenidone exposure compared to patients that do not smoke; and (e) advising the patient that smoking may result in decreased pirfenidone exposure due to the potential for smoking to induce CYP1A2 metabolism.

For the patient who smokes, the method can further comprise advising the patient to consider nicotine replacement therapy in place of smoking and/or encouraging the patent to stop smoking before treatment with pirfenidone.

In some embodiments, a method of reducing toxicity of pirfenidone treatment in a patient is provided comprising administering a therapeutically effective amount of pirfenidone to the patient and advising the patient of any of the foregoing advice.

In some embodiments, a method of improving safety of pirfenidone treatment in a patient is provided comprising administering a therapeutically effective amount of pirfenidone to the patient and advising the patient of any of the foregoing advice.

In some embodiments, a method of reducing adverse drug interaction with pirfenidone treatment in a patient (e.g., to avoid reduced exposure to pirfenidone) is provided, comprising administering a therapeutically effective amount of pirfenidone to the patient and advising the patient of any of the foregoing advice.

Thus, in some embodiments, the concomitant use or co-administration of strong CYP1A2 inducers is avoided, discontinued, or contraindicated in order to (a) avoid the potential for the altered therapeutic effect of pirfenidone, and/or (b) avoid the reduced exposure or potential for reduced exposure, and/or (c) reduce toxicity of pirfenidone treatment, and/or (d) improve safety of pirfenidone treatment, and/or (e) reduce adverse drug interaction associated with pirfenidone treatment.

In some embodiments, smoking is avoided, discontinued, or contraindicated in order to avoid the 50% decrease in pirfenidone exposure compared to patients that do not smoke.

BRIEF DESCRIPTION OF THE FIGURE

FIG. 1 depicts a symmetrical dot plot of $AUC_{0-\infty}$ estimates by study day—circles indicate smokers, triangles indicate nonsmokers.

DETAILED DESCRIPTION

Pirfenidone is an orally active, anti-fibrotic agent. Results of in vitro experiments indicated that pirfenidone is primarily metabolized by CYP1A2 (approx. 48%) with multiple other CYPs contributing as well (each <13%) (i.e., 1A1, 2A6, 2B6, 2C8, 2C9, 2C18, 2C19, 2D6, 2E1, 2J2, 3A4, 3A5, 4A11, and 4F2). Oral administration of pirfenidone results in the formation of four metabolites, 5 hydroxymethyl-pirfenidone, 5 carboxy-pirfenidone, 4'-hydroxy-pirfenidone, and the 50-acyl glucuronide metabolite of 5 carboxy-pirfenidone. In humans, only pirfenidone and 5-carboxy-pirfenidone are present in plasma in significant quantities; none of the other metabolites occur in sufficient quantities to allow for PK analysis. There are no unique human metabolites.

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration.

As used herein, a patient "in need of pirfenidone therapy" is a patient who would benefit from administration of pirfenidone. The patient may be suffering from any disease or condition for which pirfenidone therapy may be useful in ameliorating symptoms. Such diseases or conditions include pulmonary fibrosis, idiopathic pulmonary fibrosis, idiopathic interstitial pneumonia, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis; diabetic nephropathy; irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as multiple sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases.

As used herein, the term "avoid" and forms thereof are contemplated to have as alternatives the terms abstain, desist, forbear, and refrain, and forms thereof. As used herein, the term "discontinue" and forms thereof are contemplated to have as alternatives the terms cease, stop, suspend, and quit.

Preferably, a CYP inducer that metabolizes pirfenidone or a strong inducer of CYP1A2 is one that decreases plasma AUC values of pirfenidone by 30% or more. A strong CYP inducer that metabolizes pirfenidone, e.g., a strong inducer of CYP1A2, is preferably one that decreases plasma AUC values of pirfenidone by 50% or more.

In some embodiments, the effect of a CYP inducer on metabolism of pirfenidone in an individual patient is normalized based upon the patient's body surface area (BSA). BSA can be calculated using a patient's height and weight. In specific embodiments, the normalized effect of the CYP inducer is an at least 30% or at least 50% decrease in AUC values of pirfenidone.

CYP Inducers

In any of the embodiments described herein, including but not limited to the pirfenidone for use in treating a patient, the use of pirfenidone in the manufacture of a medicament for treating a patient in need of pirfenidone therapy, treatment methods involving the advice, warnings, discontinuation or dose titration downwards, the packages and kits, and/or the methods of preparing or packaging pirfenidone, the pirfenidone, uses, methods, packages, kits, advice, warnings, discontinuation or dose titration may apply not only to smoking but also to any other activity or drug that induces a CYP that metabolizes pirfenidone, including CYP1A2. The CYP inducer can be charbroiled meats or cruciferous vegetables. Additionally or alternatively, the CYP inducer can be one or more of phenobarbital, phenyloin, primidone, or St. John's wort. Additionally or alternatively, the CYP inducer can be one or more of carbamazepine, esomeprazole, griseofulvin, insulin, lansprazole, moricizine, omeprazole, rifampin, or ritonavir.

Avoiding, Discontinuing or Contraindicating Administration of a CYP Inducer to Avoid Adverse Drug Interactions with Pirfenidone (E.G., to Avoid Reduced Exposure to Pirfenidone)

In some aspects, the invention provides a method of administering pirfenidone therapy to a patient in need of pirfenidone therapy or pirfenidone for use in treating a patient in need of pirfenidone therapy (e.g., a patient with IPF), involving administering to the patient a therapeutically effective amount of pirfenidone, and avoiding use or administration (e.g., concomitant use or co-administration) of a CYP inducer that metabolizes pirfenidone (e.g., CYP1A2). In some embodiments, the CYP inducer is smoking (e.g., inhalation of the smoke of burning organic material, particularly tobacco or marijuana), as the result of polycyclic aromatic hydrocarbons which are contained in such smoke.

In other aspects, the invention provides a method of administering pirfenidone therapy to a patient in need of pirfenidone therapy, or pirfenidone for use in treating a patient in need of pirfenidone therapy, comprising discontinuing administration (e.g. co-administration) of a drug that is a CYP1A2 inducer to avoid an adverse drug interaction (e.g., to avoid reduced exposure to pirfenidone), and administering a therapeutically effective amount of pirfenidone.

In one example, in a method of administering a therapeutically effective amount of pirfenidone to a patient with IPF, or pirfenidone for use in treating a patient in need of pirfenidone therapy, the invention provides an improvement that comprises avoiding or discontinuing administration (e.g., concomitant use or co-administration) of a CYP inducer and administering a therapeutically effective amount of pirfenidone.

In some embodiments, the CYP inducer is discontinued concurrent with starting administration of pirfenidone. In other embodiments, the CYP inducer is discontinued within at least 3 days prior to starting pirfenidone therapy. In another embodiment, the CYP inducer can be discontinued within up to 4 weeks prior to starting pirfenidone therapy. In another embodiment, the CYP inducer is discontinued within 3 days after starting pirfenidone therapy, optionally up to 4 weeks after starting pirfenidone therapy. These time periods, for example, can permit adequate time for tapering and withdrawal without adverse effects.

In embodiments in which the CYP inducer is discontinued to avoid an adverse drug interaction (e.g., to avoid reduced exposure to pirfenidone), the CYP inducer preferably is discontinued within at least 3 days prior to starting pirfenidone therapy. In various embodiments, the CYP inducer is discontinued within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, prior to starting pirfenidone therapy. In some embodiments, the CYP inducer is discontinued no earlier than one month, 3 weeks, 2 weeks or 1 week before starting pirfenidone therapy. Preferably, sufficient time is allowed for tapering and/or withdrawal of the CYP inducer.

In embodiments where the CYP inducer cannot be or is not discontinued prior pirfenidone therapy, the CYP inducer is preferably discontinued within at least 3 days after starting pirfenidone therapy. In various embodiments, the CYP inducer is discontinued within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, after starting pirfenidone therapy. In some embodiments, the CYP inducer is discontinued no later than one month, 3 weeks, 2 weeks or 1 week after starting pirfenidone therapy.

In embodiments in which the patient discontinues smoking to avoid an adverse drug interaction (e.g., to avoid reduced exposure to pirfenidone), the smoking preferably is discontinued within at least 3 days prior to starting pirfenidone therapy. In various embodiments, the patient discontinues smoking within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, prior to starting pirfenidone therapy. In some embodiments, the patient discontinues smoking no earlier than one month, 3 weeks, 2 weeks or 1 week before starting pirfenidone therapy. Preferably, sufficient time is allowed for tapering and/or withdrawal of the smoking.

In embodiments in which the patient cannot or does not discontinue smoking prior to pirfenidone therapy, the smoking preferably is discontinued within at least 3 days after starting pirfenidone therapy. In various embodiments, the patient discontinues smoking within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, after starting pirfenidone therapy. In some embodiments, the patient discontinues smoking no later than one month, 3 weeks, 2 weeks or 1 week after starting pirfenidone therapy.

The patient preferably avoids use of the CYP inducer to allow sufficient time for the full dose of pirfenidone to be substantially absorbed by the patient's body. Pirfenidone has a serum half life in humans of about 2 to 3 hours. Thus, the patient preferably avoids use of the CYP inducer, for example, for at least 2.5 hours after administration of the pirfenidone. The patient can also avoid use of the CYP inducer for at least 3 hours, at least 3.5 hours, at least 4 hours, at least 4.5 hours, or at least 5 hours after administration of the pirfenidone. For example in embodiments where the patient is a smoker, the patient can avoid smoking for at least 2.5 hours, at least 3 hours, at least 3.5 hours, at least 4 hours, at least 4.5 hours, or at least 5 hours after administration of the pirfenidone. Similarly, the patient preferably avoids use of the CYP inducer for at least 1, 2, 3, or 4 serium half-lives of the CYP inducer prior to use of pirfenidone.

Selecting an Alternative Drug or Therapy to Administer Concurrently with Pirfenidone Therapy In some aspects, the invention provides a method of administering pirfenidone therapy to a patient in need of pirfenidone therapy and in need of therapy with a drug that is a CYP inducer, such as an inducer of CYP1A2, comprising administering a therapeutically effective amount of pirfenidone to the patient, and administering an alternative therapy that is not a CYP inducer.

In other aspects, the invention provides a method of administering pirfenidone therapy to a patient who smokes and in need of pirfenidone therapy, comprising administering a therapeutically effective amount of pirfenidone to the patient, and administering a stop-smoking therapy, for example nicotine replacement therapy. The nicotine replacement therapy can be any nicotine source and can include a nicotine patch, a nicotine gum, a nicotine lozenge, a nicotine nasal spray, and a nicotine inhaler. Additionally or alternatively, the method can include administration of a drug to assist in smoking cessation. Non-limiting examples of smoking cessation drugs include, but are not limited to, bupropion hydrochloride (Zyban®) or varenicline (Chantix®).

Improving Administration of Pirfenidone by Advising or Cautioning Patient

The administration of a therapeutically effective amount of pirfenidone to a patient in need of pirfenidone therapy can be improved. In some embodiments, the patient is advised that co-administration of pirfenidone with a CYP inducer that metabolizes pirfenidone can alter the therapeutic effect or adverse reaction profile of pirfenidone (e.g., can reduce exposure to pirfenidone). In some embodiments, the patient is advised that administration of pirfenidone and smoking can alter the therapeutic effect or adverse reaction profile of pirfenidone (e.g., can reduce exposure to pirfenidone).

In some embodiments, the patient is advised that co-administration of pirfenidone with a drug that is a CYP1A2 inducer can alter the therapeutic effect or adverse reaction profile of pirfenidone (e.g., can reduce exposure to pirfenidone). In some embodiments, the patient is advised that co-administration of pirfenidone with a CYP1A2 inducer can alter the therapeutic effect or adverse reaction profile of pirfenidone (e.g., can reduce exposure to pirfenidone).

In some embodiments, the patient is advised that use of pirfenidone in patients who smoke can alter the therapeutic effect or adverse reaction profile of pirfenidone (e.g., can reduce exposure to pirfenidone). In some embodiments, the patient is advised that use of pirfenidone in patients who smoke resulted in or can result in a 50% decrease in exposure to pirfenidone.

Dosing and Dose Modifications

In various embodiments, a method of administering pirfenidone and a CYP inducer that metabolizes pirfenidone (e.g., CYP1A2) is provided wherein the patient is administered a therapeutically effective amount of the inducer and a dosage of pirfenidone that is increased relative to a patient not taking the inducer. In some aspects, such an increased dosage of pirfenidone is greater than 2400 mg/day. For example, the increased dosage is about 2670 mg per day, 2937 mg per day, 3204 mg per day, 3471 mg per day, or 3738 mg per day (e.g., 10, 11, 12, 13, or 14 capsules per day where each capsule is approximately 267 mg), or higher. In another example, the dosage is increased from about 2400 mg or 2403 mg per day to about 4800 mg or 4806 mg per day. In some embodiments, the patient is already being administered the CYP inducer. In other embodiments, the patient is already being administered pirfenidone. In related embodiments, the dosage of pirfenidone is increased prior to administration of the CYP inducer.

In embodiments wherein the patient avoids or discontinues use of the CYP inducer, preferably the amount of pirfenidone being administered is at least 1800 mg, or 2400 or 2403 mg/day. Pirfenidone can be dosed at a total amount of about 2400 mg to about 3800 mg or 4800 mg per day. The dosage can be divided into two or three doses over the day or given in a single daily dose. Specific amounts of the total daily amount of the therapeutic contemplated for the disclosed methods include about 2400 mg, about 2450 mg, about 2500 mg, about 2550 mg, about 2600 mg, about 2650 mg, about 2670 mg, about 2700 mg, about 2750 mg, about 2800 mg, about 2850 mg, about 2900 mg, about 2937 mg, about 2950 mg, about 3000 mg, about 3050 mg, about 3100 mg, about 3150 mg, about 3200 mg, about 3204 mg, about 3250 mg, about 3300 mg, about 3350 mg, about 3400 mg, about 3450 mg, about 3471 mg, about 3500 mg, about 3550 mg, about 3600 mg, about 3650 mg, about 3700 mg, about 3738 mg, about 3750 mg, and about 3800 mg.

Dosages of pirfenidone can alternately be administered as a dose measured in mg/kg. Contemplated mg/kg doses of the disclosed therapeutics include about 1 mg/kg to about 40 mg/kg. Specific ranges of doses in mg/kg include about 1 mg/kg to about 20 mg/kg, about 5 mg/kg to about 20 mg/kg, about 10 mg/kg to about 20 mg/kg, about 10 mg/kg to about 30 mg/kg, and about 15 mg/kg to about 25 mg/kg. Other specific ranges of doses include about 1 mg/kg to about 35 mg/kg. Specific doses contemplated include about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg.

In one aspect of a use or method described herein, a dosage amount of pirfenidone is taken with food. In another aspect, the patient is instructed to administer the dosage of pirfenidone with food.

In some embodiments, a method of optimizing pirfenidone therapy is provided comprising titrating the dosage of pirfenidone administered to a patient upward relative to a previously administered dosage in the patient, wherein co-administration of a CYP inducer that metabolizes pirfenidone to the patient does not result in a decreased exposure to pirfenidone. In some embodiments, the dose is increased by about 100 mg/day. In other embodiments, the dose is increased by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day, or about 1650 mg/day, or about 1700 mg/day, or about 1750 mg/day, or about 1800 mg/day, or about 1850 mg/day, or about 1900 mg/day, or about 1950 mg/day, or about 2000 mg/day, or about 2050 mg/day, or about 2100 mg/day, or about 2150 mg/day, or about 2200 mg/day, or about 2250 mg/day, or about 2300 mg/day, or about 2350 mg/day, or about 2400 mg/day or more. For example, the dosage is increased from about 2400 mg or 2403 mg per day to about 4800 mg or 4806 mg per day. As another example, the dosage is increased from about 1800 mg per day to about 3600 mg per day.

In some embodiments, a method of optimizing pirfenidone therapy is provided comprising titrating the dosage of pirfenidone administered to a patient upward relative to a previously administered dosage in the patient, wherein co-administration of a drug that is an inducer of CYP1A2 to the patient does not result in a decreased exposure to pirfenidone. In some embodiments, the dose is increased by about 100 mg/day. In other embodiments, the dose is increased by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day, or about 1650 mg/day, or about 1700 mg/day, or about 1750 mg/day, or about 1800 mg/day, or about 1850 mg/day, or about 1900 mg/day, or about 1950 mg/day, or about 2000 mg/day, or about 2050 mg/day, or about 2100 mg/day, or about 2150 mg/day, or about 2200 mg/day, or about 2250 mg/day, or about 2300 mg/day, or about 2350 mg/day, or about 2400 mg/day or more. For example, the dosage is increased from about 2400 mg or 2403 mg per day to about 4800 mg or 4806 mg per day. As another example, the dosage is increased from about 1800 mg per day to about 3600 mg per day.

In some embodiments, a method of optimizing pirfenidone therapy is provided comprising titrating the dosage of pirfenidone administered to a patient upward relative to a previously administered dosage in the patient, wherein co-administration of a CYP1A2 inducer to the patient does not result in a decreased exposure to pirfenidone. In some embodiments, the dose is increased by about 100 mg/day. In other embodiments, the dose is increased by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day, or about 1650 mg/day, or about 1700 mg/day, or about 1750 mg/day, or about 1800 mg/day, or about 1850 mg/day, or about 1900 mg/day, or about 1950 mg/day, or about 2000 mg/day, or about 2050 mg/day, or about 2100 mg/day, or about 2150 mg/day, or about 2200 mg/day, or about 2250 mg/day, or about 2300 mg/day, or about 2350 mg/day, or about 2400 mg/day or more. For example, the dosage is increased from about 2400 mg or 2403 mg per day to about 4800 mg or 4806 mg per day. As another example, the dosage is increased from about 1800 mg per day to about 3600 mg per day.

Packages, Kits, Methods of Packaging, and Methods of Delivering

In another aspect, a package or kit is provided comprising pirfenidone, optionally in a container, and a package insert, package label, instructions or other labeling including any one, two, three or more of the following information or recommendations:

(a) advising the patient that strong CYP inducers that metabolize pirfenidone should be avoided or discontinued;

(b) advising the patient that smoking should be avoided or discontinued;

(c) advising the patient that co-administration of pirfenidone with a CYP inducer that metabolizes pirfenidone can alter the therapeutic effect of pirfenidone;

(d) advising the patient that administration of pirfenidone in patients that smoke results in a 50% decrease in pirfenidone exposure compared to patients that do not smoke; and (e) advising the patient that smoking may result in decreased pirfenidone exposure due to the potential for smoking to induce CYP1A2 metabolism. In some embodiments, the information or recommendation may include that co-administration of pirfenidone with inducers of CYP that metabolize pirfenidone can alter the therapeutic effect or adverse reaction profile of pirfenidone (e.g., can reduce exposure to pirfenidone). In other embodiments, the information or recommendation may include that administration of pirfenidone to a patient who smokes can alter the therapeutic effect or adverse reaction profile of pirfenidone (e.g., can reduce exposure to pirfenidone). In other embodiments, the information or recommendation may include that co-administration of pirfenidone with CYP1A2 inducers can alter the therapeutic effect or adverse reaction profile of pirfenidone (e.g., can reduce exposure to pirfenidone).

In other embodiments, the information or recommendation may include that drugs that are CYP1A2 inducers should be avoided. In other embodiments, the information or recommendation may include that drugs that are CYP1A2 inducers should be discontinued. It is understood that such avoiding and/or discontinuing by a manufacturer, distributor, or seller of pirfenidone can be a contraindication. In other embodiments, the information or recommendation may include that drugs that are CYP1A2 inducers should be used with caution. In yet other embodiments, the information or recommendation may be any of the regimens for titrating the dosage of pirfenidone administered to a patient upward relative to a previously administered dosage in the patient, as described above.

The package insert, package label, instructions or other labeling may further comprise directions for treating IPF by administering pirfenidone, e.g., at a dosage of at least 1800 mg, or 2400 mg or 2403 mg per day.

In related aspect, the invention provides a method of preparing or packaging a pirfenidone medicament comprising packaging pirfenidone, optionally in a container, together with a package insert or package label or instructions including any one, two, three or more of the foregoing information or recommendations.

In some embodiments, a method of treating IPF is disclosed comprising providing, selling or delivering any of the kits of disclosed herein to a hospital, physician or patient.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

An open-label Phase 1 study was performed to determine the impacts of a strong CYP1A2 inhibitor and a CYP1A2 inducer on the pharmacokinetics and safety of pirfenidone in healthy subjects.

Study Design.

The study was a Phase 1, open-label, parallel-group study designed to investigate the impact of CYP1A2 inhibition and induction on the pharmacokinetics and safety of pirfenidone in healthy subjects. Fifty-four subjects were to be enrolled in two groups, consisting of 27 subjects who were smokers (Group 1) and 27 subjects who were nonsmokers (Group 2). Each group (smokers and nonsmokers) was to include a minimum of nine females and nine males, and attempts were to be made to enroll equal numbers of each sex in each group. Each subject was to receive a single 801-mg dose of pirfenidone on Days 1 and 11. Fluvoxamine dosing was started on Day 2 and titrated to the final dose according to the following schedule:

Days 2-4: fluvoxamine 50 mg at bedtime
Days 5-7: fluvoxamine 50 mg twice a day (in the morning and at bedtime)
Days 8-11: fluvoxamine 50 mg in the morning and 100 mg at bedtime All pharmacokinetic (PK) analyses were conducted using population PK methods using Monte-Carlo parametric expectation maximization as implemented in the open-source software program S ADAPT 1.5.6 (Bauer et al., *AAPS Journal* 9 (1):E60-83, 2007). The structural model for the analysis was obtained from a preliminary population PK analysis. This population PK model was fit to the pirfenidone and 5 carboxy-pirfenidone plasma concentration-time data from Days 1 and 11 separately. Once a final population PK model was defined, $AUC_{0-\infty}$ estimates were generated by simulating plasma PK profiles and compared for statistically significant differences between days (to test the effect of fluvoxamine co-administration) and between groups (to test the effect of smoking).

As the primary endpoint of the study, differences in the pirfenidone and 5 carboxy pirfenidone $AUC_{0-\infty}$ estimates between Days 1 and 11, and between smokers and nonsmokers were tested for significance. The analysis of the effect of fluvoxamine (i.e., Day 1 versus Day 11) was analyzed using the FDA criteria for bioequivalence for paired data (FDA 2003). The ratio of $AUC_{0-\infty}$ on Day 11 to that on Day 1 was used to test for the interaction between smoking status and fluvoxamine coadministration. If other subject characteristics (such as body size or age) were also associated with the ratio of $AUC_{0-\infty}$ on Day 11 to that on Day 1, the significance of these covariates was also tested. The significance of differences in pirfenidone and 5-carboxy-pirfenidone $AUC_{0-\infty}$ estimates on Day 1 in smokers and nonsmokers was tested using multivariable linear regression in order to take into account the effects of other significant covariates.

Pharmacokinetic Results.

Fifty-one of the 54 subjects enrolled in the study were included in the PK analyses. Three subjects were removed from the PK analyses as they did not meet the protocol-specified requirement for adequate compliance with the fluvoxamine dosing regimen. Two subjects discontinued the study early due to adverse events, and one subject only took 73% of the protocol-required fluvoxamine dose. All 51 subjects had the full complement of PK samples available for analysis. Each subject had two profiles on each day: one for pirfenidone and one for 5 carboxy pirfenidone. There were a total of 1224 samples (12 per subject per day); each sample was assayed for pirfenidone and 5 carboxy-pirfenidone for a total of 2448 concentrations.

A robust fit to the data was obtained using the population PK structural model. In general, the fits of the data were excellent: 98% of the individual profiles had $r^2$ values above 0.9 and there was no systematic bias in the fits.

The summary statistics of $AUC_{0-\infty}$ stratified by study day are provided in Table 1. Symmetrical dot density plots of pirfenidone and 5 carboxy pirfenidone $AUC_{0-\infty}$ values versus study day, identified by smoking status, are provided in FIG. 1. The co-administration of fluvoxamine resulted in a significant increase in the $AUC_{0-\infty}$ of pirfenidone (p<0.00001). There was not a statistically significant effect of fluvoxamine co-administration on 5 carboxy pirfenidone $AUC_{0-\infty}$.

TABLE 1

Comparison of $AUC_{0-\infty}$ Between Study Days (n = 51)

| | | $AUC_{0-\infty}$ (mg · hr/L) | |
|---|---|---|---|
| Study Day | Statistic | Pirfenidone[a] | 5-Carboxy-Pirfenidone[b] |
| 1: Pre-Fluvoxamine | Mean (SD) | 34.9 (16.9) | 29.3 (8.22) |
| | Median (25th-75th) | 34.7 (21.4-45.9) | 26.9 (22.0-33.7) |
| 11: Post-Fluvoxamine | Mean (SD) | 171 (47.7) | 31.7 (8.96) |
| | Median (25th-75th) | 167 (126-206) | 29.4 (25.4-36.5) |

[a] p-value <0.00001 (paired t-test)
[b] p-value = 0.168 (paired t-test)
$AUC_{0-\infty}$ = area under the concentration-time curve from time zero to infinity;
SD = standard deviation.

There was also a large apparent difference in the $C_{max}$ estimates pre- and post-fluvoxamine; the pirfenidone $C_{max}$ was higher after administration of fluvoxamine while the 5 carboxy pirfenidone $C_{max}$ was lower after administration of fluvoxamine. The mean (95% CI) for the ratio of $C_{max}$ on Day 11 to the $C_{max}$ on Day 1 was 2.09 (1.94-2.25) for pirfenidone and 0.369 (0.349-0.390) for 5-carboxy-pirfenidone.

The summary statistics of the ratio of the $AUC_{0-\infty}$ on Day 11 to the $AUC_{0-\infty}$ on Day 1, stratified by smoking status, are provided in Table 2. While both smokers and nonsmokers were affected by the coadministration of fluvoxamine, smokers appeared to have a more pronounced increase in exposure to pirfenidone, as evidenced by the higher ratio of Day 11 to Day 1 AUC. Given that there was an imbalance in the demographics between smokers and nonsmokers (smokers were younger, heavier and predominantly male), the impact of these variables on the ratio of the pirfenidone $AUC_{0-\infty}$ on Day 11 to the $AUC_{0-\infty}$ on Day 1 was tested using multiple linear regression. Using backward elimination (p-value for removal=0.10), smoking status was the only significant predictor of the ratio of the pirfenidone $AUC_{0-\infty}$ on Day 11 to the $AUC_{0-\infty}$ on Day 1; body size, sex, and age were not significant.

TABLE 2

Comparison of Ratio of Day 11 $AUC_{0-\infty}$ to Day 1 $AUC_{0-\infty}$ by Smoking Status

| Smoking Status | Statistic | Pirfenidone | 5-Carboxy-Pirfenidone |
|---|---|---|---|
| Smokers | N | 26 | 26 |
| | Mean (SD) | 7.32 (2.12) | 1.12 (0.0951) |
| | Median (25th-75th) | 7.07 (6.12-8.25) | 1.13 (1.04-1.19) |

TABLE 2-continued

Comparison of Ratio of Day 11 $AUC_{0-\infty}$ to Day 1 $AUC_{0-\infty}$ by Smoking Status

| Smoking Status | Statistic | Pirfenidone | 5-Carboxy-Pirfenidone |
|---|---|---|---|
| Nonsmokers | N | 25 | 25 |
| | Mean (SD) | 4.13 (1.15) | 1.05 (0.114) |
| | Median ($25^{th}$-$75^{th}$) | 3.99 (3.26-4.68) | 1.03 (0.978-1.11) |

$AUC_{0-\infty}$ = area under the concentration-time curve from time zero to infinity;
SD = standard deviation.

The relationship between smoking status and exposure to pirfenidone and 5 carboxy pirfenidone were examined using the $AUC_{0-\infty}$ estimates from Day 1. Due to the high degree of correlation between BSA and other demographic variables (sex, creatinine clearance (mL/min) (CLcr), age) and the pharmacologic plausibility of a relationship between exposure and body size, $AUC_{0-\infty}$ was first normalized to body surface area before application of multiple linear regression. Smoking status was the only significant predictor of the variability in pirfenidone $AUC_{0-\infty}$ normalized to BSA. Smoking status had a pronounced effect in that smokers would be predicted to have a ~50% drop in $AUC_{0-\infty}$ after accounting for differences in BSA. For 5 carboxy-pirfenidone $AUC_{0-\infty}$, the only significant predictors were age and CLcr.

In summary, the design and execution of this study allowed for a robust and informative analysis of the effects of CYP1A2 inhibition and/or induction on the pharmacokinetics of pirfenidone. Administration of the potent CYP inhibitor fluvoxamine resulted in a significant drug interaction and markedly increased pirfenidone exposure. Smokers were likely to experience significantly lower pirfenidone exposure (in the absence of the drug interaction) presumably due to the inductive effects of smoking.

The coadministration of fluvoxamine resulted in a significant drug interaction such that exposure ($AUC_{0-\infty}$) to pirfenidone was, on average, nearly 6 times higher after ten days of dosing with fluvoxamine Subjects also experienced, on average, a two-fold increase in $C_{max}$ after administration of fluvoxamine.

Administration of pirfenidone to patients who smoke resulted in a significant decrease in exposure ($AUC_{0-\infty}$) to pirfenidone, and was, on average, about 50% the exposure of pirfenidone in patients that didn't smoke.

While the present invention has been described in terms of various embodiments and examples, it is understood that variations and improvements will occur to those skilled in the art. Therefore, only such limitations as appear in the claims should be placed on the invention.

Examples of Embodiments of the Invention Include

1. A method of administering pirfenidone therapy to a patient in need thereof comprising administering to the patient a therapeutically effective amount of pirfenidone and avoiding use or administration of a strong inducer of a cytochrome P450 (CYP) that metabolizes pirfenidone.

2. The method of paragraph 1, wherein the strong inducer of CYP is avoided for at least 2.5 hours after administration of the pirfenidone.

3. The method of paragraph 2, wherein the patient is a smoker and avoids smoking for at least 2.5 hours after administration of the pirfenidone.

4. A method of administering pirfenidone therapy to a patient in need thereof, wherein the patient is receiving an inducer of a cytochrome P450 (CYP) that metabolizes pirfenidone, comprising discontinuing use or administration of the inducer of a cytochrome P450 (CYP) that metabolizes pirfenidone to avoid an adverse drug reaction and administering a therapeutically effective amount of pirfenidone.

5. The method of paragraph 4, wherein the inducer of CYP is discontinued prior to administration of pirfenidone.

6. The method of paragraph 5, wherein the inducer of CYP is discontinued within 4 weeks prior to the administration of pirfenidone.

7. The method of paragraph 4, wherein the inducer of CYP is discontinued concurrent to administration of pirfenidone.

8. The method of paragraph 1 or 4, wherein the patient is a smoker, comprising discontinuing smoking.

9. The method of paragraph 8, further comprising administering a nicotine replacement therapy to the patient.

10. The method of paragraph 9, wherein the nicotine replacement therapy comprises one or more of a nicotine patch, a nicotine gum, a nicotine lozenge, a nicotine nasal spray, and a nicotine inhaler.

11. The method of paragraph 8, further comprising administering to the patient bupropion hydrochloride (Zyban) or varenicline (Chantix).

12. A method of administering pirfenidone therapy to a patient in need thereof, comprising administering to the patient a therapeutically effective amount of pirfenidone, and any one or more of the following:
  (a) advising the patient that strong inducers of a cytochrome P450 (CYP) that metabolizes pirfenidone should be avoided or discontinued;
  (b) advising the patient that smoking should be avoided or discontinued;
  (c) advising the patient that co-administration of pirfenidone with an inducer of CYP that metabolizes pirfenidone can alter the therapeutic effect of pirfenidone;
  (d) advising the patient that administration of pirfenidone in patients that smoke results in a 50% decrease in pirfenidone exposure compared to patients that do not smoke; and
  (e) advising the patient that smoking may result in decreased pirfenidone exposure due to the potential for smoking to induce CYP1A2 metabolism.

13. The method of paragraph 12, wherein the patient is a smoker, and further comprising advising the patient to consider nicotine replacement therapy in place of smoking.

14. The method of any one of paragraphs 12-13, further comprising encouraging patients who smoke to stop smoking before treatment with pirfenidone.

15. The method of any one of paragraphs 1-14, wherein the therapeutically effective amount of pirfenidone is a total daily dose of about 2400 mg.

16. The method of any one of paragraphs 1-15, wherein the pirfenidone is administered three times a day, at a total daily dose of about 2400 mg.

17. The method of any one of paragraphs 1-16, wherein the CYP comprises CYP1A2.

18. The method of any one of paragraphs 1-17, wherein the patient suffers from idiopathic pulmonary fibrosis (IPF).

19. The method of any one of paragraphs 1-18, wherein the pirfenidone is co-administered with food.

20. The method of any one of paragraphs 1-19, wherein the inducer of a cytochrome P450 (CYP) that metabolizes pirfenidone is one or more of carbamazepine, charbroiled food, cigarette smoke, cruciferous vegetables, esomeprazole, griseofulvin, insulin, lansprazole, marijuana smoke, moricizine, omeprazole, phenobarbital, phenyloin, primidone rifampin, ritonavir, smoking, and St. John's wort.

Other Examples of Embodiments of the Invention Include

1A. A method of administering pirfenidone therapy to a patient in need thereof, wherein the patient is a smoker, comprising discontinuing smoking to avoid an adverse drug reaction and administering a therapeutically effective amount of pirfenidone.
2A. The method of paragraph 1A, wherein the patient discontinues smoking within 4 weeks prior to the administration of pirfenidone.
3A. The method of paragraph 1A, wherein the patient discontinues smoking concurrent to administration of pirfenidone.
4A. The method of paragraph 1A, comprising discontinuing smoking to avoid an adverse drug reaction which is decreased exposure to pirfenidone.
5A. The method of paragraph 1A, further comprising advising the patient that administration of pirfenidone in patients that smoke results in a 50% decrease in pirfenidone exposure compared to patients that do not smoke.
6A. The method of paragraph 1A, wherein the patient has idiopathic pulmonary fibrosis.
7A. The method of paragraph 1A, wherein the therapeutically effective amount of pirfenidone is 2400 mg or 2403 mg per day.
8A. A method of administering pirfenidone therapy to a patient in need thereof comprising administering to the patient a therapeutically effective amount of pirfenidone and avoiding use or administration of a strong inducer of a cytochrome P450 1A2 (CYP1A2) to avoid an adverse drug reaction.
9A. The method of paragraph 8A, comprising avoiding use or administration of a strong inducer of CYP1A2 to avoid an adverse drug reaction which is reduced exposure to pirfenidone.
10A. The method of paragraph 8A, wherein the patient is a smoker and avoids smoking when using pirfenidone.
11A. The method of paragraph 8A, wherein the patient has idiopathic pulmonary fibrosis.
12A. The method of paragraph 8A, wherein the therapeutically effective amount of pirfenidone is 2400 mg or 2403 mg per day.
13A. A method of administering pirfenidone therapy to a patient in need thereof, comprising administering to the patient a therapeutically effective amount of pirfenidone, and one or more of the following:
  (a) advising the patient that inducers of a cytochrome P450 (CYP) (CYP1A2) should be avoided or discontinued;
  (b) advising the patient that smoking should be avoided when using pirfenidone due to the potential for smoking to induce CYP1A2 metabolism resulting in decreased exposure to pirfenidone;
  (c) advising the patient that smoking should be discontinued before treatment with pirfenidone;
  (d) advising the patient that administration of pirfenidone in patients that smoke results in a 50% decrease in pirfenidone exposure compared to patients that do not smoke; and
  (e) advising the patient that smoking may result in decreased pirfenidone exposure due to the potential for smoking to induce CYP1A2 metabolism.
14A. The method of paragraph 13A, further comprising encouraging patients who smoke to stop smoking before treatment with pirfenidone.
15A. The method of paragraph 13A, expedient (a), comprising advising the patient that strong inducers of a CYP1A2 should be avoided or discontinued.
16A. The method of paragraph 13A, wherein the inducer of a CYP1A2 is one or more of carbamazepine, charbroiled food, cigarette smoke, cruciferous vegetables, esomeprazole, griseofulvin, insulin, lansprazole, marijuana smoke, moricizine, omeprazole, phenobarbital, phenyloin, primidone rifampin, ritonavir, smoking, and St. John's wort.
17A. The method of paragraph 16A, wherein the CYP1A2 inducer is selected from the group consisting of carbamazepine, esomeprazole, griseofulvin, insulin, lansprazole, moricizine, omeprazole, rifampin, ritonavir, and smoking.
18A. The method of paragraph 16A, wherein the CYP1A2 inducer is selected from the group consisting of carbamazepine, lansoprazole, omeprazole, phenobarbital, phenyloin, primidone, rifampin, ritonavir, smoking, and St. John's wort.
19A. The method of paragraph 13A, wherein the patient in need of pirfenidone therapy is treated for idiopathic pulmonary fibrosis.
20A. The method of paragraph 13A, wherein the therapeutically effective amount of pirfenidone is 2400 mg or 2403 mg per day.

Still Other Examples of Embodiments of the Invention Include

1B. Pirfenidone for use in treating a patient in need of pirfenidone therapy, characterized in that the treating comprises avoiding or discontinuing concomitant use or co-administration of a strong inducer of cytochrome P450 1A2 (CYP1A2) to avoid reduced exposure to pirfenidone.
2B. The use of pirfenidone in the manufacture of a medicament for treating a patient in need of pirfenidone therapy, characterized in that the treating comprises avoiding or discontinuing concomitant use or co-administration of a strong inducer of cytochrome P450 1A2 (CYP1A2) to avoid reduced exposure to pirfenidone.
3B. The pirfenidone or use of any one of paragraphs 1B to 2B characterized in that the treating comprises avoiding concomitant use or co-administration of a strong inducer of cytochrome P450 1A2 (CYP1A2).
4B. The pirfenidone or use of any one of paragraphs 1B to 2B wherein the patient is avoiding concomitant use or co-administration of a strong inducer of cytochrome P450 1A2 (CYP1A2).
5B. The pirfenidone or use of any one of paragraphs 1B to 2B wherein the patient is a smoker who is discontinuing smoking to avoid reduced exposure to pirfenidone.
6B. The pirfenidone or use of paragraph 5B wherein the patient is discontinuing smoking within 4 weeks prior to the administration of pirfenidone.
7B. The pirfenidone or use of paragraph 5B wherein the patient is discontinuing smoking concurrent with the start of administration of pirfenidone.
8B. The pirfenidone or use of any one of paragraphs 1B to 2B wherein the patient is a smoker and avoids smoking when using pirfenidone.
9B. The pirfenidone or use of any one of paragraphs 1B to 4B wherein the inducer of a CYP1A2 is one or more of carbamazepine, charbroiled food, cigarette smoke, cruciferous vegetables, esomeprazole, griseofulvin, insulin, lansprazole, marijuana smoke, moricizine, omeprazole, phenobarbital, phenyloin, primidone rifampin, ritonavir, smoking, and St. John's wort.

10B. The pirfenidone or use of any one of paragraphs 1B to 9B wherein the patient suffers from a disease selected from pulmonary fibrosis, idiopathic pulmonary fibrosis, idiopathic interstitial pneumonia, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute or chronic renal disease; renal fibrosis; diabetic nephropathy; irritable bowel syndrome; pyresis; restenosis; cerebral malaria; stroke or ischemic injury; neural trauma; Alzheimer's disease; Huntington's disease; Parkinson's disease; acute or chronic pain; allergies, including allergic rhinitis or allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, or non-small cell lung cancer; graft-versus-host reaction; or autoimmune diseases, such as multiple sclerosis, lupus or fibromyalgia; AIDS or other viral diseases such as Herpes Zoster, Herpes Simplex I or II, influenza virus, Severe Acute Respiratory Syndrome (SARS) or cytomegalovirus; or diabetes mellitus, proliferative disorders (including both benign or malignant hyperplasias), acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases; pain disorders including neuromuscular pain, headache, cancer pain, dental pain, or arthritis pain; angiogenic disorders including solid tumor angiogenesis, ocular neovascularization, or infantile hemangioma; conditions associated with the cyclooxygenase or lipoxygenase signaling pathways, including conditions associated with prostaglandin endoperoxide synthase-2 (including edema, fever, analgesia, or pain); organ hypoxia; thrombin-induced platelet aggregation; or protozoal diseases.

11B. The pirfenidone or use of any one of paragraphs 1B to 10B wherein the patient has idiopathic pulmonary fibrosis.

12B. The pirfenidone or use of any one of paragraphs 1B to 11B wherein the pirfenidone is administered at a total daily dosage of 2400 mg or 2403 mg per day.

13B. The pirfenidone or use of any one of paragraphs 1B to 12B, wherein each dose of pirfenidone administered is 801 mg.

14B. Pirfenidone for use in treating a patient in need of pirfenidone therapy, characterized in that the treating comprises administering pirfenidone to the patient and contraindicating, avoiding or discontinuing a strong inducer of cytochrome P450 1A2 (CYP1A2) to avoid reduced exposure to pirfenidone.

15B. A package or kit comprising (a) pirfenidone, optionally in a container, and (b) a package insert, package label, instructions or other labeling comprising contraindicating, avoiding, or discontinuing concomitant use or co-administration of a strong inducer of cytochrome P450 1A2 (CYP1A2), and optionally according to any of the embodiments of paragraphs 1B-14B or as described anywhere above.

What is claimed is:

1. A method of increasing the effectiveness of pirfenidone therapy by avoiding decreased exposure to pirfenidone, in a patient in need of pirfenidone therapy and taking a strong inducer of cytochrome P450 1A2 (CYP1A2), comprising administering to the patient a therapeutically effective amount of pirfenidone, and avoiding the strong inducer of a cytochrome P450 1A2 (CYP1A2).

2. The method of claim 1, wherein the patient has idiopathic pulmonary fibrosis.

3. The method of claim 1, wherein the patient suffers from a fibrosis condition.

4. The method of claim 1, wherein the pirfenidone is administered at a total daily dosage of at least 1800 mg.

5. The method of claim 2, wherein the pirfenidone is administered at a total daily dosage of at least 1800 mg.

6. The method of claim 1, wherein the pirfenidone is administered at a total daily dosage of 2400 mg or 2403 mg.

7. The method of claim 2, wherein the pirfenidone is administered at a total daily dosage of 2400 mg or 2403 mg.

8. The method of claim 1, wherein each dose of pirfenidone administered is 801 mg.

9. The method of claim 6, wherein pirfenidone is administered three times a day.

10. The method of claim 9, wherein pirfenidone is administered with food.

11. The method of claim 1, wherein the strong CYP1A2 inducer is cigarette smoke.

12. The method of claim 11, wherein the patient has idiopathic pulmonary fibrosis.

13. The method of claim 11, wherein the patient suffers from a fibrosis condition.

14. The method of claim 11, wherein the pirfenidone is administered at a total daily dosage of at least 1800 mg.

15. The method of claim 12, wherein the pirfenidone is administered at a total daily dosage of at least 1800 mg.

16. The method of claim 11, wherein the pirfenidone is administered at a total daily dosage of 2400 mg or 2403 mg.

17. The method of claim 12, wherein the pirfenidone is administered at a total daily dosage of 2400 mg or 2403 mg.

18. The method of claim 16, wherein pirfenidone is administered three times a day.

19. The method of claim 18, wherein pirfenidone is administered with food.

* * * * *